(12) United States Patent
Eddins

(10) Patent No.: US 6,170,282 B1
(45) Date of Patent: Jan. 9, 2001

(54) PORTABLE AIR CONDITIONER

(76) Inventor: Garey L. Eddins, 445 Sycamore St., Jemison, AL (US) 35085

( * ) Notice: Under 35 U.S.C. 154(b), the term of this patent shall be extended for 0 days.

(21) Appl. No.: 09/383,680

(22) Filed: Aug. 26, 1999

(51) Int. Cl.[7] .............................. F25D 23/12; F25D 3/08
(52) U.S. Cl. ....................... 62/259.3; 62/457.1; 62/457.2
(58) Field of Search .................................. 62/457.1, 457, 62/2, 459, 420, 259.3; 165/122

(56) References Cited

U.S. PATENT DOCUMENTS

| 4,841,742 | * | 6/1989 | Biby | ........................ | 62/420 |
| 5,046,329 | * | 9/1991 | Travis | ................................ | 62/259.3 |
| 5,062,281 | * | 11/1991 | Oliphant et al. | ..................... | 62/457.1 |
| 5,737,938 | * | 4/1998 | Liu | ................................ | 62/457.2 X |

* cited by examiner

Primary Examiner—William Doerrler
Assistant Examiner—Chen-Wen Jiang

(57) ABSTRACT

A portable air conditioner for personal use wherever needed. The portable air conditioner includes an insulated housing in the shape of a box. A lid is removably attached to a top of the housing. An intake portal is located in the housing. A first tube is in fluid connection with the intake portal. The tube extends into the housing perpendicular to the first side of the housing and arcs away from the lid. A discharge portal is located in the housing. A second tube extends into the housing whereby the second tube is in fluid connection with the discharge portal. The second tube extends perpendicular to the second side of the housing. The second tube arcs away from the lid. A fan draws air into intake portal. A power source is operationally coupled to the fan.

20 Claims, 3 Drawing Sheets

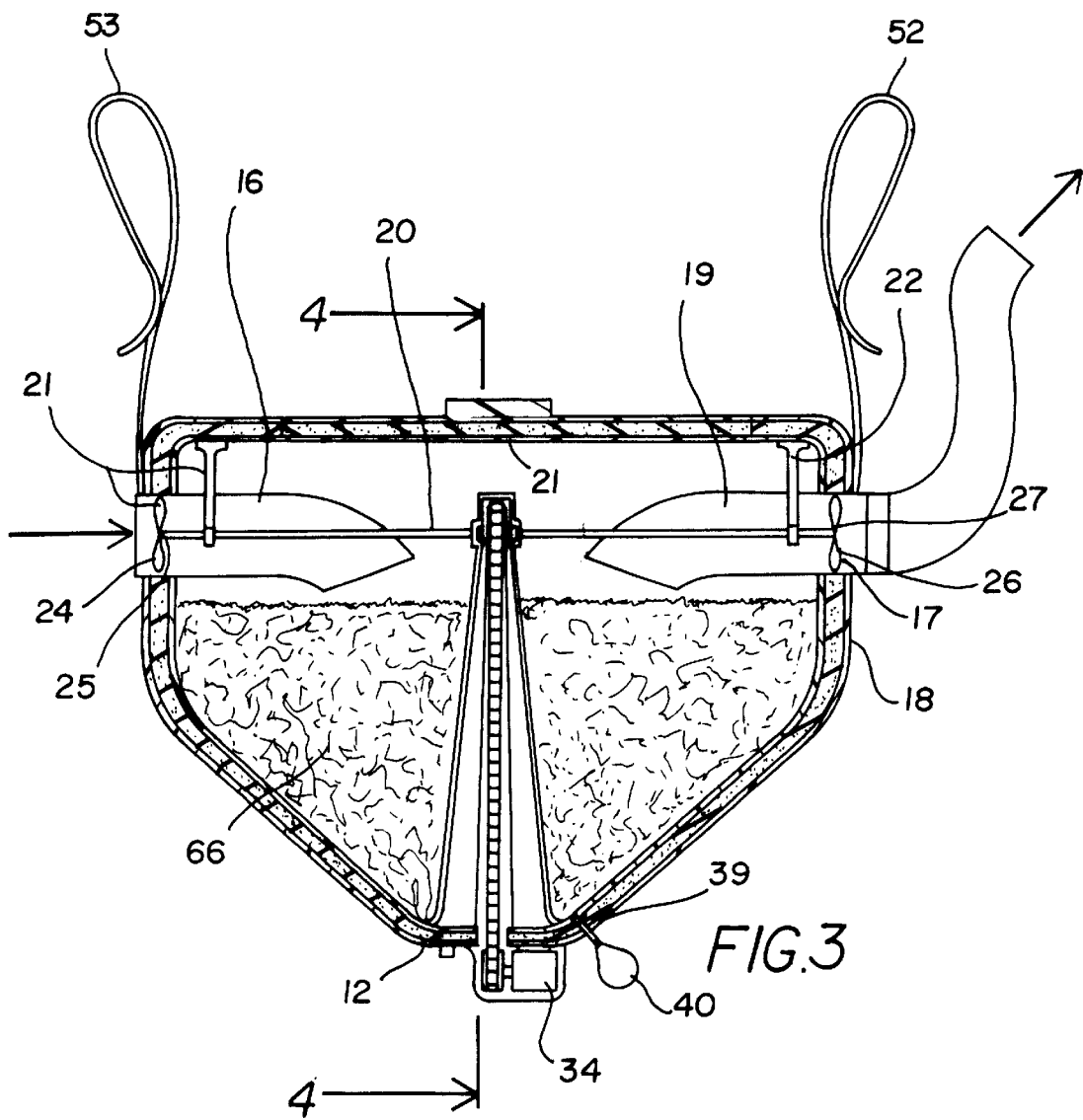

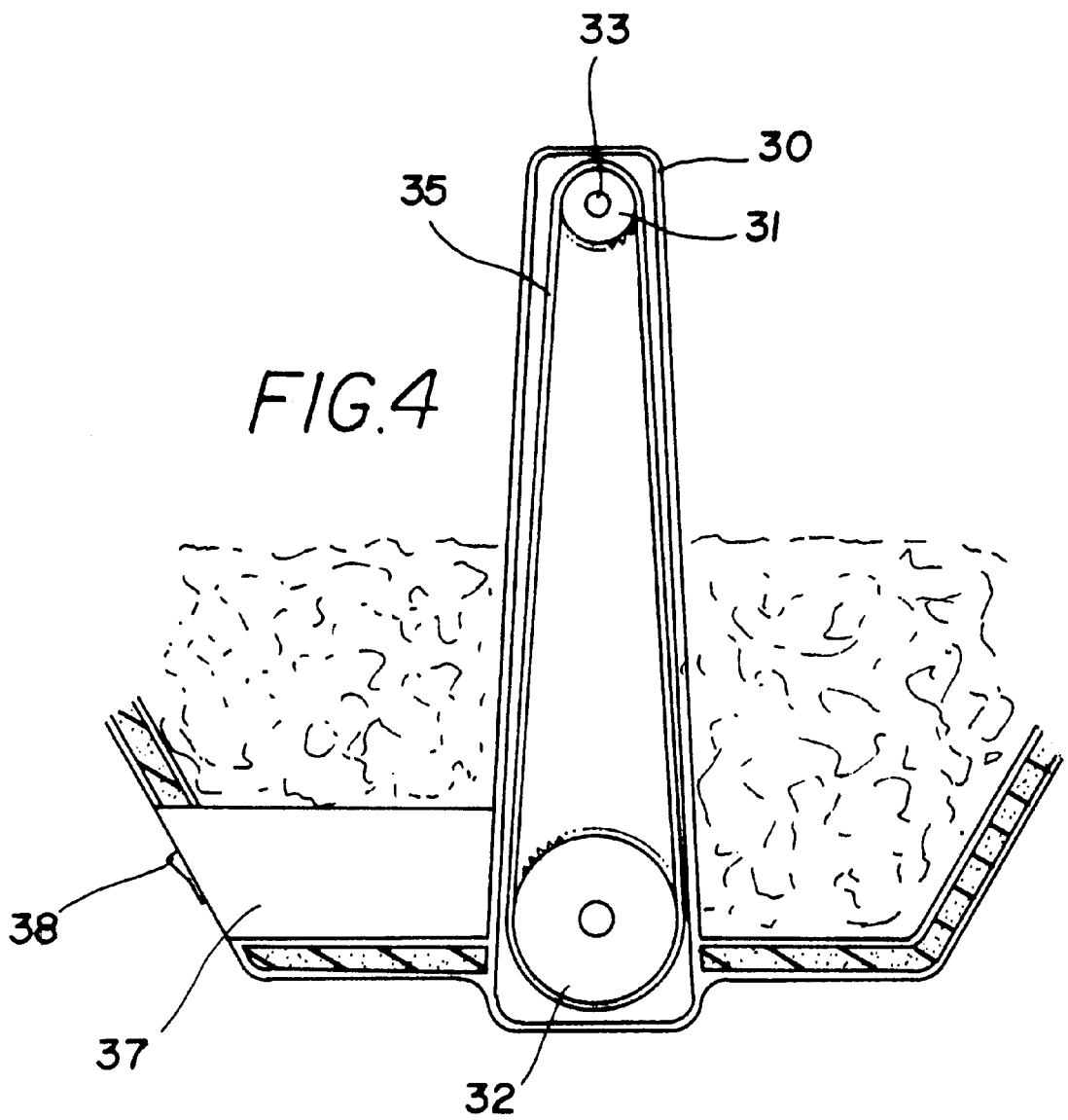

PORTABLE AIR CONDITIONER

BACKGROUND OF THE INVENTION

1. Field of the Invention

The present invention relates to air conditioners and more particularly pertains to a new portable air conditioner for personal use wherever needed.

2. Description of the Prior Art

The use of air conditioners is known in the prior art. More specifically, air conditioners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,685,165; U.S. Pat. No. 4,841,742; U.S. Pat. No. 5,197,301; U.S. Pat. No. Des. 306,062; U.S. Pat. No. 2,080,998; and U.S. Pat. No. 3,529,435.

While these devices fulfill their respective, particular objectives and requirements, the aforementioned patents do not disclose a new portable air conditioner. The inventive device includes an insulated housing in the shape of a box. A lid is removably attached to a top of the housing. An intake portal is located in the housing. A first tube is in fluid connection with the intake portal. The tube extends into the housing perpendicular to the first side of the housing and arcs away from the lid. A discharge portal is located in the housing. A second tube extends into the housing whereby the second tube is in fluid connection with the discharge portal. The second tube extends perpendicular to the second side of the housing. The second tube arcs away from the lid. A fan draws air into intake portal. A power source is operationally coupled to the fan.

In these respects, the portable air conditioner according to the present invention substantially departs from the conventional concepts and designs of the prior art, and in so doing provides an apparatus primarily developed for the purpose of personal use wherever needed.

SUMMARY OF THE INVENTION

In view of the foregoing disadvantages inherent in the known types of air conditioners now present in the prior art, the present invention provides a new portable air conditioner construction wherein the same can be utilized for personal use wherever needed.

The general purpose of the present invention, which will be described subsequently in greater detail, is to provide a new portable air conditioner apparatus and method which has many of the advantages of the air conditioners mentioned heretofore and many novel features that result in a new portable air conditioner which is not anticipated, rendered obvious, suggested, or even implied by any of the prior art air conditioners, either alone or in any combination thereof.

To attain this, the present invention generally comprises an insulated housing in the shape of a box. A lid is removably attached to a top of the housing. An intake portal is located in the housing. A first tube is in fluid connection with the intake portal. The tube extends into the housing perpendicular to the first side of the housing and arcs away from the lid. A discharge portal is located in the housing. A second tube extends into the housing whereby the second tube is in fluid connection with the discharge portal. The second tube extends perpendicular to the second side of the housing. The second tube arcs away from the lid. A fan draws air into intake portal. A power source is operationally coupled to the fan.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new portable air conditioner apparatus and method which has many of the advantages of the air conditioners mentioned heretofore and many novel features that result in a new portable air conditioner which is not anticipated, rendered obvious, suggested, or even implied by any of the prior art air conditioners, either alone or in any combination thereof.

It is another object of the present invention to provide a new portable air conditioner which may be easily and efficiently manufactured and marketed.

It is a further object of the present invention to provide a new portable air conditioner which is of a durable and reliable construction.

An even further object of the present invention is to provide a new portable air conditioner which is susceptible of a low cost of manufacture with regard to both materials and labor, and which accordingly is then susceptible of low prices of sale to the consuming public, thereby making such portable air conditioner economically available to the buying public.

Still yet another object of the present invention is to provide a new portable air conditioner which provides in the apparatuses and methods of the prior art some of the advantages thereof, while simultaneously overcoming some of the disadvantages normally associated therewith.

Still another object of the present invention is to provide a new portable air conditioner for personal use wherever needed.

Yet another object of the present invention is to provide a new portable air conditioner which includes an insulated housing in the shape of a box. A lid is removably attached to a top of the housing. An intake portal is located in the housing. A first tube is in fluid connection with the intake portal. The tube extends into the housing perpendicular to the first side of the housing and arcs away from the lid. A discharge portal is located in the housing. A second tube extends into the housing whereby the second tube is in fluid connection with the discharge portal. The second tube extends perpendicular to the second side of the housing. The second tube arcs away from the lid. A fan draws air into intake portal. A power source is operationally coupled to the fan.

Still yet another object of the present invention is to provide a new portable air conditioner that is of light weight and can be carried on the users back to allow the cooled air to blow upon the user's face and neck.

Even still another object of the present invention is to provide a new portable air conditioner that can be set down in a stand for use inside of a tent or other areas where the user does not need to carry the air conditioner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic cross-sectional view taken along line 3—3 of the present invention.

FIG. 4 is a schematic cross-sectional view along line 4—4 of the present invention.

DESCRIPTION OF THE PREFERRED EMBODIMENT

Figure 1:
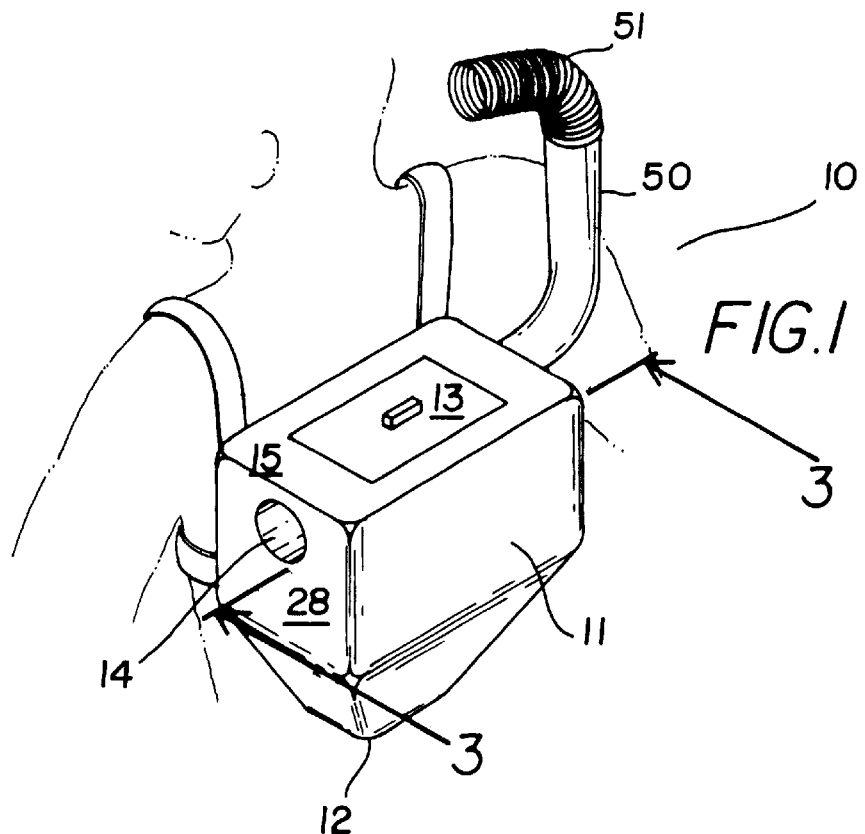
FIG. 1 is a schematic perspective view of a new portable air conditioner according to the present invention.
Figure 2:
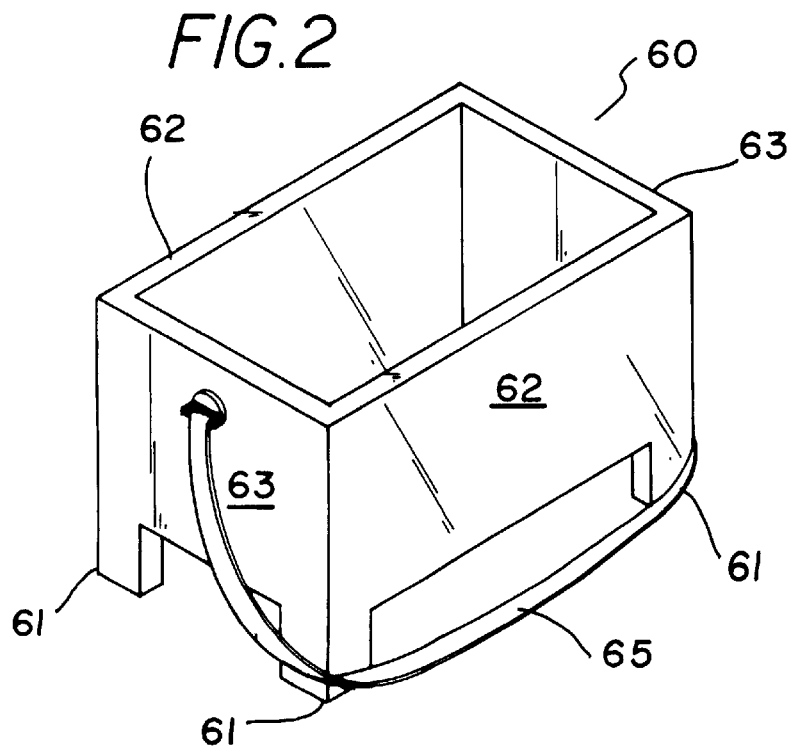
FIG. 2 is a schematic perspective view of a stand for the present invention.

With reference now to the drawings, and in particular to FIGS. 1 through 4 thereof, a new portable air conditioner embodying the principles and concepts of the present invention and generally designated by the reference numeral 10 will be described.

As best illustrated in FIGS. 1 through 4, the portable air conditioner 10 generally comprises an insulated housing 11, in the shape of a box wherein a bottom portion 12 of the housing extends downwardly in the shape of a frustum. The housing can be made from any insulating material, however polystyrene is preferred due to its light weight. A lid 13 is in a top side 15 of the housing. An intake portal 14 is on the first side 28 of the housing and is substantially adjacent to the top side of the housing. A first tube 16 is in fluid connection with the intake portal and extends into the housing. The first tube extends perpendicular to the first side of the housing. The first tube arcs away from the lid. A discharge portal 17 is on a second side 18 of the housing. The second side is parallel to the first side of the housing. The discharge portal is substantially adjacent to the top side of the housing. A second tube 19 extends into the housing whereby the second tube is in fluid connection with the discharge portal. The second tube extends perpendicular to the second side of the housing and gradually arcs away from the lid.

A bar 20 is mounted to a bottom side 21 of the top portion 15 of the housing. The mounting is comprised of two elongate members 22, 23 extending downwardly from opposite sides of the bottom side of the top portion. The mountings are adapted to allow the bar to rotate on an axial center line. The bar extends from the intake portal 14 to the discharge portal 17. A first propeller 24 is attached to the first end 25 of the bar. The first propeller is angled to draw air into the housing. A second propeller 26 is attached to second end 27 of the bar. The second propeller is angled to pull air from the housing.

A gear housing 30 contains a first gear 31 and a second gear 32. The first gear is coupled to the bar through a bore 33 in the gear. The second gear is coupled to an electric motor 34. The motor is mounted to the housing and, as it is coupled to the second gear, it holds the second gear in place. The first gear and the second gear are coupled together by a belt 35. The housing and the mounting for the bar hold the first gear in place. Preferably, the motor is located at a tip of the frustum 12. Preferably, a battery 37 is operationally coupled to the motor. Also preferably, a switch 38 is located adjacent to the battery and is operationally coupled thereto to turn the motor off and on.

A drain 39 is located adjacent to the motor. Preferably the draining means comprises a bore in the housing and a pin 40 adapted to be removably placed in the bore.

A duct 50 is affixed to the discharge portal 17 and extends away from the housing. Preferably, the duct has a flexible portion 51 thereon for directing airflow.

Two straps 52, 53 are attached a third side (not shown) of the housing.

Optionally, the portable unit can come with a stand 60. The stand being adapted to hold the portable air conditioner. The stand being rectangular in shape wherein each of the corners of the stand has a leg 61 extending downwardly therefrom. The stand has two sets 62, 63 of parallel upwardly extending walls. One set of parallel walls 63 has a third strap 65 attached therebetween for carrying the stand.

In use, the lid 13 is opened and ice 66 is placed inside of the housing. The switch 38 is turned on which activates the motor 34. The power supply is ideally a battery pack 37, but another embodiment, not shown, would utilize a conventional power supply comprising a plug and standard home outlet with a motor adapted for AC current. The motor turns the bottom gear 32 and a belt 35 attached to it turns the top gear 31 . The top gear is coupled to the bar 20 which rotates causing the propellers 24, 26 to turn. The action of the first propeller 24 draws air into the housing. The second propeller 26 is not necessary but is preferably included, as it will push the air out of the housing at a greater velocity than if the first propeller were working alone. The air is drawn over the ice 66 that cools it down. The cool air leaves through the discharge portal 17 and enters the duct 50. The duct is fitted with a portion 51 that is bendable to allow the user to direct the cool air in any direction. The housing has straps 52, 53 attached to it to allow users to wear the unit on their backs. Optionally, a stand 60 comes with the unit to allow the user to sit the unit down next to them such as for use in a tent. A drainage pin 40 allows excess water to be removed from the unit.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A portable air conditioner comprising:
    an insulated housing, said housing being in the shape of a box;
    a lid removably attached to a top of said housing;
    an intake portal in said housing, said intake portal being on a first side of said housing;
    a first tube in fluid connection with said intake portal, said tube extending into said housing, said first tube extending perpendicular to said first side of said housing, said first tube arcing away from said lid;
    a discharge portal in said housing;
    a second tube, said second tube extending into said housing whereby said second tube is in fluid connection with said discharge portal, said second tube extending perpendicular to said second side of said housing, said second tube arcing away from said lid;
    a fan means adapted to draw air into said intake portal;
    a power source operationally coupled to said fan means; and
    two straps, said straps being attached to a third side of said housing, said straps adapted to hold said housing to a user.

2. The portable air conditioner as stated in claim 1, wherein a bottom portion of said housing extends to define a frustum.

3. The portable air conditioner as stated in claim 2, wherein said fan means comprises:
    a bar, said bar extending from said intake portal to said discharge portal;
    a first propeller, said first propeller being attached to a first end of said bar, said first propeller angled to draw air into said housing;
    a second propeller, said second propeller being attached to second end of said bar, said second propeller angled to pull air from said housing;
    a gear housing, said gear housing containing a first gear and a second gear, said first gear being coupled to said bar, said second gear being coupled to a motor means, said first gear and said second gear being coupled together by a belt, said motor being located at a tip of said frustum, wherein said power source is a battery.

4. The portable air conditioner as stated in claim 3, and further comprising a draining means, said draining means being located adjacent to said motor, said draining means comprising a bore in said housing and a pin adapted to be removably placed in said bore.

5. The portable air conditioner as stated in claim 1, wherein said intake portal being orientated in a first side of said housing, said intake portal being substantially adjacent to said top side of said housing.

6. The portable air conditioner as stated in claim 5, wherein said discharge portal being on a second side of said housing, said second side being parallel to said first side of said housing, said discharge portal being substantially adjacent to said top side of said housing.

7. The portable air conditioner as stated in claim 1, and further comprising a duct, said duct being affixed to said discharge portal, said duct extending away from said housing, said duct having a flexible portion thereon for directing airflow.

8. The portable air conditioner as stated in claim 7 and further comprising a stand, said stand being adapted to hold said portable air conditioner, said stand being rectangular in shape, said stand having four corners wherein each of said corners of said stand has a leg extending downwardly therefrom, said stand having two sets of parallel upwardly extending walls, one set of said parallel walls having a third strap attached therebetween for carrying said stand.

9. A portable air conditioner comprising:
    an insulated housing, said housing being rectangular wherein a bottom portion of said housing extends downwardly in the shape of a frustum;
    a lid, said lid being in a top side of said housing;
    an intake portal in said housing, said intake portal being on a first side of said housing, said intake portal being substantially adjacent to said top side of said housing;
    a first tube in fluid connection with said intake portal, said tube extending into said housing, said first tube extending perpendicular to said first side of said housing, said first tube arcing away from said lid;
    a discharge portal, said discharge portal being in a second side of said housing, said second side being parallel to said first side of said housing, said discharge portal being substantially adjacent to said top side of said housing;
    a second tube, said second tube extending into said housing whereby said second tube is in fluid connection with discharge portal, said second tube extending perpendicular to said second side of said housing, said second tube arcing away from said lid;
    a fan means adapted to draw air into said housing through said intake portal;
    a power source operationally coupled to said fan means;
    a draining means, said draining means being located in said frustum of said housing, said draining means comprising a bore in said housing and a pin adapted to be removably placed in said bore; and
    a duct, said duct being affixed to said discharge portal, said duct extending away from said housing, said duct having a flexible portion thereon for directing airflow.

10. The portable air condition as stated in claim 9, further comprising two straps, said straps being attached to a third side of said housing, said straps adapted to hold said housing to a user.

11. The portable air conditioner as stated in claim 9, wherein said fan means comprises:
    a bar, said bar being mounted to a bottom side of said top portion of said housing, said mounting being comprised of two elongate members extending downwardly from opposite sides of said bottom side of said top portion, said mountings adapted to allow said bar to rotate on a axial center line, said bar extending from said intake portal to said discharge portal;

a first propeller, said first propeller being attached to a first end of said bar, said first propeller angled to draw air into said housing;

a second propeller, said second propeller being attached to second end of said bar, said second propeller angled to pull air from said housing;

a gear housing, said gear housing containing a first gear and a second gear, said first gear being coupled to said bar, said second gear being coupled to a motor means, said first gear and said second gear being coupled together by a belt, said motor being located at a tip of said frustum, wherein said power source is a battery.

12. The portable air conditioner as stated in claim 9 and further comprising a stand, said stand being adapted to hold said portable air conditioner, said stand being rectangular in shape, said stand having four corners wherein each of said corners of said stand has a leg extending downwardly therefrom, said stand having two sets of parallel upwardly extending walls, one set of said parallel walls having a third strap attached therebetween for carrying said stand.

13. A portable air conditioner comprising:

an insulated housing, said housing being in the shape of a box wherein a bottom portion of said housing extends downwardly in the shape of a frustum;

a lid, said lid being in a top side of said housing;

an intake portal in said housing, said intake portal being on a first side of said housing, said intake portal being substantially adjacent to said top side of said housing;

a first tube in fluid connection with said intake portal, said tube extending into said housing, said first tube extending perpendicular to said first side of said housing, said first tube arcing away from said lid;

a discharge portal, said discharge portal being on a second side of said housing, said second side being parallel to said first side of said housing, said discharge portal being substantially adjacent to said top side of said housing;

a second tube, said second tube extending into said housing whereby said second tube is in fluid connection with said discharge portal, said second tube extending perpendicular to said second side of said housing, said second tube arcing away from said lid;

a bar, said bar being mounted to a bottom side of said top portion of said housing, said mounting being comprised of two elongate members extending downwardly from opposite sides of said bottom side of said top portion, said mountings adapted to allow said bar to rotate on a axial center line, said bar extending from said intake portal to said discharge portal;

a first propeller, said first propeller being attached to a first end of said bar, said first propeller angled to draw air into said housing, a second propeller, said second propeller being attached to second end of said bar, said second propeller angled to pull air from said housing;

a gear housing, said gear housing containing a first gear and a second gear, said first gear being coupled to said bar, said second gear being coupled to a motor means, said first gear and said second gear being coupled together by a belt, said motor being located at a tip of said frustum;

a battery, said battery being operationally coupled to said motor;

a draining means, said draining means being located adjacent to said motor, said draining means comprising a bore in said housing and a pin adapted to be removably placed in said bore;

a duct, said duct being affixed to said discharge portal, said duct extending away from said housing, said duct having a flexible portion thereon for directing airflow; and two straps, said straps being attached a third side of said housing.

14. The portable air conditioner as stated in claim 13 and further comprising a stand, said stand being adapted to hold said portable air conditioner, said stand being rectangular in shape, said stand having four corners wherein each of said corners of said stand has a leg extending downwardly therefrom, said stand having two sets of parallel upwardly extending walls, one set of said parallel walls having a third strap attached therebetween for carrying said stand.

15. A portable air conditioner comprising:

an insulated housing, said housing being in the shape of a box;

a lid removably attached to a top of said housing;

an intake portal in said housing, said intake portal being on a first side of said housing;

a first tube in fluid connection with said intake portal, said tube extending into said housing, said first tube extending perpendicular to said first side of said housing, said first tube arcing away from said lid;

a discharge portal in said housing;

a second tube, said second tube extending into said housing whereby said second tube is in fluid connection with said discharge portal, said second tube extending perpendicular to said second side of said housing, said second tube arcing away from said lid;

a fan means adapted to draw air into said intake portal;

a power source operationally coupled to said fan means; and wherein a bottom portion of said housing extends to define a frustum.

16. The portable air conditioner as stated in claim 15, wherein said intake portal being orientated in a first side of said housing, said intake portal being substantially adjacent to said top side of said housing.

17. The portable air conditioner as stated in claim 16, wherein said discharge portal being on a second side of said housing, said second side being parallel to said first side of said housing, said discharge portal being substantially adjacent to said top side of said housing.

18. The portable air conditioner as stated in claim 15, wherein said fan means comprises:

a bar, said bar extending from said intake portal to said discharge portal;

a first propeller, said first propeller being attached to a first end of said bar, said first propeller angled to draw air into said housing;

a second propeller, said second propeller being attached to second end of said bar, said second propeller angled to pull air from said housing;

a gear housing, said gear housing containing a first gear and a second gear, said first gear being coupled to said bar, said second gear being coupled to a motor means, said first gear and said second gear being coupled together by a belt, said motor being located at a tip of said frustum, wherein said power source is a battery.

19. The portable air conditioner as stated in claim 18, and further comprising a draining means, said draining means being located adjacent to said motor, said draining means comprising a bore in said housing and a pin adapted to be removably placed in said bore.

20. The portable air conditioner as stated in claim 15, and further comprising a duct, said duct being affixed to said discharge portal, said duct extending away from said housing, said duct having a flexible portion thereon for directing airflow.

* * * * *